United States Patent [19]

Yui et al.

[11] Patent Number: 5,378,396
[45] Date of Patent: Jan. 3, 1995

[54] LIQUID CRYSTAL COMPOUND AND LIQUID CRYSTAL DISPLAY DEVICE

[75] Inventors: Tomoyuki Yui, Nagareyama; Toshio Watanabe, Tsukuba; Yoshihisa Arai, Tsukuba; Masahiro Johno, Tsukuba, all of Japan

[73] Assignee: Mitsubishi Gas Chemical Company, Inc., Tokyo, Japan

[21] Appl. No.: 235,418

[22] Filed: Apr. 22, 1994

Related U.S. Application Data

[63] Continuation of Ser. No. 795,733, Nov. 21, 1991, abandoned.

[30] Foreign Application Priority Data

Nov. 20, 1990 [JP]  Japan .................................. 2-314306

[51] Int. Cl.⁶ ..................... C09K 19/12; C09K 19/20; G02F 1/13; C07C 69/76
[52] U.S. Cl. .......................... 252/299.65; 252/299.64; 252/299.66; 359/103; 560/85; 560/102
[58] Field of Search ........... 252/299.64, 299.65, 252/299.66; 359/103; 560/85, 102

[56] References Cited

U.S. PATENT DOCUMENTS 5,116,531  5/1992  Hagiwara et al. ............. 252/299.65
5,316,694  5/1994  Murashiro et al. ............ 252/299.61

FOREIGN PATENT DOCUMENTS 0418604  3/1991  European Pat. Off. .

OTHER PUBLICATIONS

Patent Abstracts of Japan, vol. 14, No. 197 (C-712) 23 Apr. 1990 (JP-A-2 040 346).
Patent Abstracts of Japan, vol. 14, No. 115 (C-696) 5 Mar. 1990 (JP-A-1 316 347).
Chemical Abstracts 109: 14938T (1988) (JP-A-62-373,284).

Primary Examiner—Shean Wu
Attorney, Agent, or Firm—Sherman and Shalloway

[57] ABSTRACT

A liquid crystal compound represented by formula (I)

$$R-X-(C_6H_4)_K-COO-(C_6H_4)_L-COOC^*HC_nH_{2n+1} \quad (I)$$
$$\overset{|}{\underset{}{C_2H_5}}$$

wherein R denotes a linear alkyl group having 6 to 14 carbon atoms, X denotes a single bond or an oxygen atom, K and L are independently 1 or 2, n is an integer of 3 to 8, and C* denotes an asymmetric carbon atom.

and a liquid crystal display device formed therefrom.

2 Claims, 4 Drawing Sheets

LIQUID CRYSTAL COMPOUND AND LIQUID CRYSTAL DISPLAY DEVICE

This application is a continuation of application Ser. No. 07/795,733, filed Nov. 21, 1991 now abandoned.

DETAILED DESCRIPTION OF THE INVENTION

This invention relates to a novel liquid crystal compound and a liquid crystal display device. More specifically, this invention relates to a novel antiferroelectric phenyl ester-type liquid crystal compound and a liquid crystal display device using same.

PRIOR ART

Liquid crystal display devices have been to date used as various small-screen devices because a voltage is low, an electric power consumption is low and thin display is possible. Since the liquid crystal display devices have, however, recently found use in the fields of information, office automation appliances, television, etc., high-performance, large-sized liquid crystal display devices having higher resolution and higher display qualities than the ordinary CRT display devices have been increasingly demanded rapidly.

Nevertheless, so far as the present nematic liquid crystals are used as display devices, even active matrix liquid crystal display devices employed in liquid crystal television sets have difficulty to produce a large screen with low cost owing to intricacy of their production process and their low yields. Meanwhile, simple matrix STN liquid crystal display devices are not necessarily easy to drive the large screen with high quality, and the response time is also limited. Under the circumstances, at the present stage, the nematic liquid crystal display devices cannot be said to meet the demand for the high-performance, large-sized liquid crystal display devices.

PROBLEMS THE INVENTION AIMS TO SOLVE

On the other hand, liquid crystal display devices using ferroelectric liquid crystal compounds arouse interest as liquid crystal display devices having high-speed response. Surface stabilized ferroelectric liquid crystal (SSFLC) devices reported by N. A. Clark and S. T. Lagerwall are noteworthy in that they have high-speed response and a wide viewing angle that have not ever been provided [N. A. Clark and S. T. Lagerwall, Appl. Phys. Lett. 36(1980) 899].

Switching characteristics of said SSFLC devices have been studied in detail, and many ferroelectric liquid crystal compounds have been proposed to optimize various properties.

Said SSFLC devices have not been put to practical use, however, because of various factors that since threshold characteristics are not sufficient, contrast is poor, high-speed response is not realized, alignment is destroyed by mechanical shock and is hardly recovered, and so forth.

Separately, devices of switching mechanism different from SSFLC devices have been also developed at the same time. Tristable switching of liquid crystal compounds having an antiferroelectric phase (hereinafter referred to as "antiferroelectric liquid crystal compounds") are one of the new switching mechanisms (Japanese Journal of Applied Physics, vol. 27, No.5, p. L729, 1988).

Antiferroelectric liquid crystal devices (devices using antiferroelectric liquid crystal compounds) have three stable states, i.e., two uniform states (Ur, Ul) observed in the ferroelectric liquid crystal devices and a third state. The third state is an antiferroelectric phase reported by Chandani, et al (Japanese Journal of Applied Physics, vol. 28, p. L1261, 1989 and Japanese Journal of Applied Physics, vol. 28, p. L1265, 1989).

Such tristable switching is the first characteristic feature of the antiferroelectric liquid crystal devices. The second characteristic feature of the antiferroelectric liquid crystal devices is a sharp threshold against an applied voltage. The third characteristic feature thereof is memory effect. Liquid crystal display devices having high-speed response and good contrast can be realized by utilizing these excellent characteristic features.

Another great characteristic feature is that a layer structure is easily switched by an electric field (Japanese Journal of Applied Physics, vol. 28, p. L119, 1989, and Japanese Journal of Applied Physics, vol. 29, p. L111, 1990). As a result, it becomes possible to realize less defective liquid crystal display devices having an alignment self-recovering ability.

As the antiferroelectric liquid crystal compound, those described in Japanese Laid-open Patent Appln. (Kokai) Nos. 213390/1989, 316339/1989, 316367/1989, 316372/1989 and 28128/1990 and Liquid Crystals, vol. 6, No. 2, p. 167, 1989 are known. Meanwhile, studies over the antiferroelectric liquid crystal compounds have just started, and antiferroelectric liquid crystal compounds known to date are few.

It is thus a first object of this invention to provide a novel liquid crystal compound having an antiferroelectric phase.

A second object of this invention is to provide a liquid crystal compound that can be used as a liquid crystal display device having tristable switching, sharp threshold and good memory effect.

A third object of this invention is to provide a high-performance liquid crystal compound that can be used in a large-sized liquid crystal compound having high-speed response.

A fourth object of this invention is to provide a liquid crystal display device using the liquid crystal compound having the aforesaid characteristics.

The other objects of this invention will be clarified from the foregoing description.

MEANS FOR SOLVING THE PROBLEMS

According to the present inventors' studies, it is found that the aforesaid objects and advantages of this invention are achieved by a liquid crystal compound represented by formula (I)

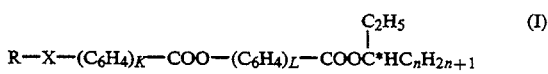

$$R-X-(C_6H_4)_K-COO-(C_6H_4)_L-COOC^*HC_nH_{2n+1} \quad (I)$$

wherein R denotes a linear alkyl group having 9 to 12 carbon atoms, X denotes a single bond or an oxygen atom, K and L are independently 1 or 2, n is an integer of 4, 6 or 8, and C* denotes an asymmetric carbon atom.

The phenyl ester compound of formula (I) in this invention will be described in more detail below.

The compound of formula (I) has in the molecule the asymmetric carbon atom (C*) to which $-C_2H_5$ is directly bonded. In formula (I), R is a linear alkyl group having 6 to 14, preferably 8 to 12 carbon atoms. X in formula (I) is a single bond or an oxygen atom. $(C_6H_4)_K$ in formula (I) is

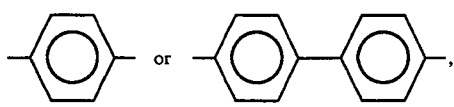

and $(C_6H_4)_L$ is likewise

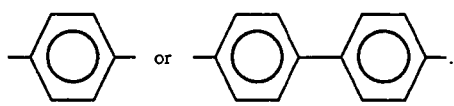

—$C_nH_{2n+1}$ is a linear alkyl group wherein n is an integer of 3 to 8.

The liquid crystal compound of formula (I) in this invention is novel and an example of a process for producing same is schematically shown below.

In the above reaction schemes (1) and (2), R, K, L, and n are as defined in formula (I), R' is a linear alkyl group having 5 to 14 carbon atoms (while R is a linear alkyl group having 6 to 14 carbon atoms).

The number of carbon atoms of the alkyl group denoted by R in the above reaction schemes influences the phase transition temperature and the melting point of the liquid crystal. When the number of carbon atoms is too small, even a liquid crystal phase is not shown. When the number of carbon atoms is too large, a temperature of a chiral smectic C phase or an antiferroelectric phase useful as a switching device is by far higher than room temperature, and a melting point becomes high; they are practically unwanted. For this reason, the number of carbon atoms of R is 6 to 14, preferably 8 to 12.

EFFECTS OF THE INVENTION

The phenyl ester-type liquid crystal compound of formula (I) in this invention has antiferroelectricity. The novel liquid crystal compound provided by this invention can be used in a liquid crystal display device utilizing the characteristics, i.e., high-speed response or tristable switching, sharp threshold and good memory effect.

EXAMPLES

Figure 1:
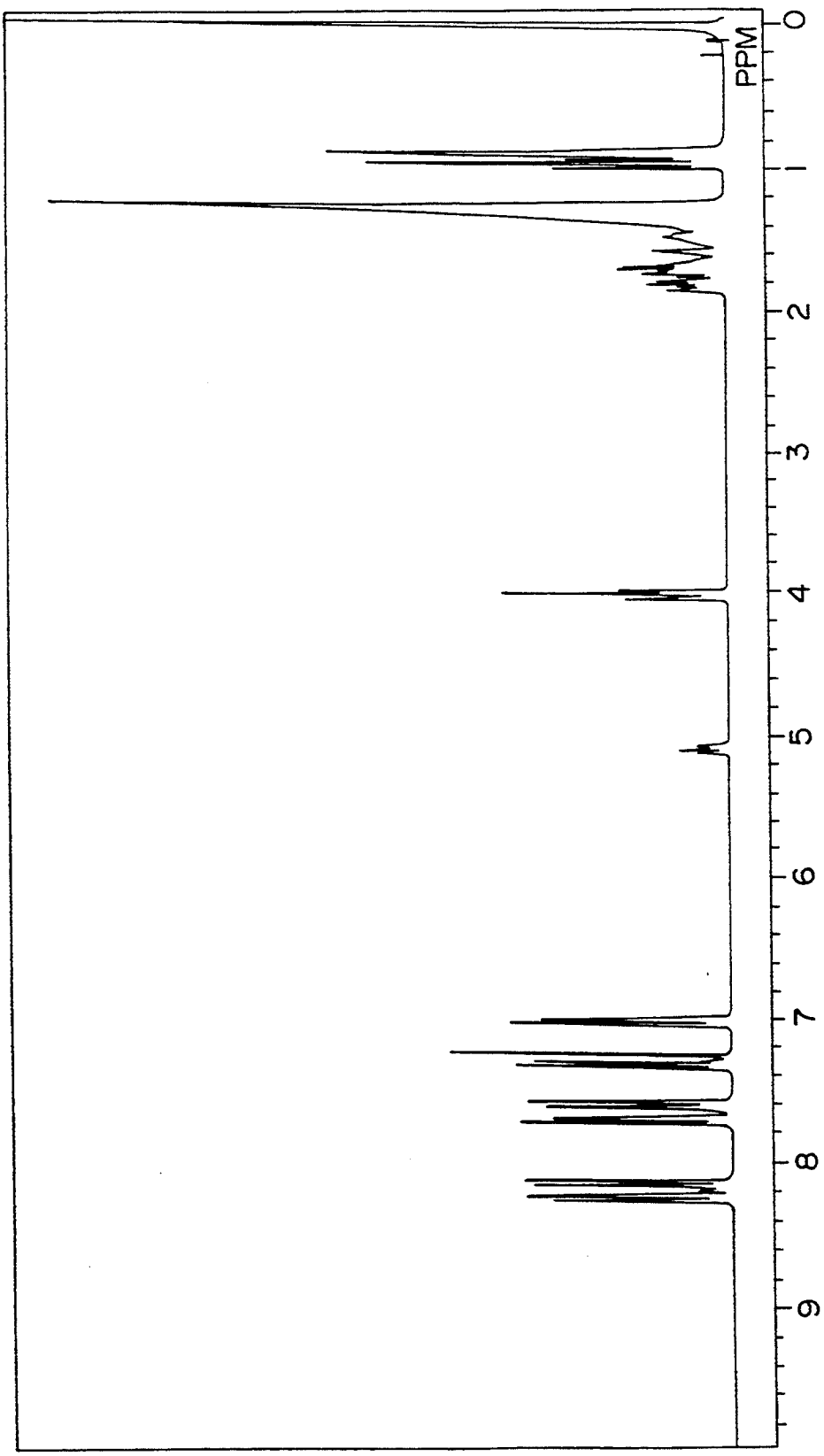
FIG. 1 is an NMR spectrum of a liquid crystal compound (4) in Example 1.

The following examples illustrate this invention more specifically. This invention is, of course, not limited thereto.

EXAMPLE 1

Production of 4-(1-ethylheptyloxycarbonylphenyl) 4'-decyloxybiphenyl-4-carboxylate [In formula (1), $R=C_{10}H_{21}$, $X=-O-$, $K=2$, $L=1$, $n=6$]

1) Production of 4-(4'-n-decyloxy)biphenylcarboxylic acid (1)

4-(4'-Hydroxy)biphenylcarboxylic acid (10.5 g), 16.2 g of n-decyl bromide and 6.45 g of potassium hydroxide were added to a mixed solution of 1,500 ml of ethanol and 200 ml of water, and reacted for 10 hours under reflux. Further, 500 ml of water was added, and the mixture was stirred for 3 hours. After the reaction was over, the reaction mixture was acidified with conc. hydrochloric acid. Then, 500 ml of the solvent was evaporated, and the residue was cooled to room temperature to obtain a white solid. Said solid was thoroughly washed with water and recrystallized from chloroform to obtain 13.1 g of a final product (1) as a white crystal.

2) Production of 4-acetoxy-1-(1-ethylheptyloxycarbonyl)benzene (2)

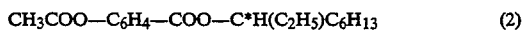

4-Acetoxybenzoic acid (3.5 g) was added to 25 ml of thionyl chloride, and the reaction was run for 10 hours under reflux. After excess thionyl chloride was evaporated, 10 ml of pyridine and 50 ml of toluene were added, and 2.2 g of optically active S-(+)-3-nonanol was added dropwise thereto. After the dropwise addition, the mixture was refluxed for 4 hours, allowed to cool and diluted with 500 ml of dichloromethane. The organic layer was washed with dilute hydrochloric acid, a 1N sodium hydroxide aqueous solution and water in this sequence, and dried over magnesium sulfate. The solvent was evaporated to obtain 1.9 g of a crude final product (2).

3) Production of 4-hydroxy-1-(1-ethylheptyloxycarbonyl)benzene (3)

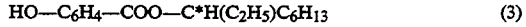

The crude final product (2) (1.9 g) was dissolved in 50 ml of ethanol, and 4 g of benzylamine was added dropwise. The mixture was stirred at room temperature for 4 hours, then diluted with 500 ml of chloroform, washed with dilute hydrochloric acid and water in this sequence, and dried over magnesium sulfate. After the solvent was evaporated, the solid was purified by silica gel column chromatography to obtain 1.1 g of a final product (3).

4) Production of 4-(1-ethylheptyloxycarbonylphenyl) 4'-n-decyloxybiphenyl-4-carboxylate (4)

Ten milliliters of thionyl chloride were added to 1.0 g of the compound (1) and refluxed for 10 hours. After excess thionyl chloride was evaporated, 10 ml of pyridine and 60 ml of toluene were added, and 20 ml of a toluene solution of 0.5 g of the compound 3 was then added dropwise, followed by the reaction at room temperature for 10 hours. After the reaction was over, the reaction mixture was diluted with 500 ml of chloroform, washed with dilute hydrochloric acid, a 1N sodium hydroxide aqueous solution and water in this sequence. The organic layer was dried over magnesium sulfate.

After the solvent was evaporated, the solid was purified by silica gel column chromatography. The purified solid was then recrystallized with ethanol to obtain 0.6 g of a final product (4). An NMR spectrum of the final product (4) is shown in FIG. 1. Identification of phases was carried out by observation of a texture and measurement with DSC (differential scanning calorimeter).

Phase transition temperatures of the compound (4) are as follows. In the compound (4), an antiferroelectric phase was observed in a wide temperature range.

wherein $S_A$ and $S_{CA^*}$ are a smectic A phase and an antiferroelectric phase, respectively.

5) A liquid crystal cell (a cell thickness 3 micrometers) with an ITO electrode having a rubbed polyimide thin film was filled with the compound (4) in an isotropic phase. The cell was slowly cooled at a rate of 1.0° C. per minute, and the liquid crystal was aligned in a $S_A$ phase. The cell was disposed between intersecting deflection plates such that the layer direction of the liquid crystal was parallel to an analyzer or a polarizer. A triangular wave voltage of ±40 V and 0.2 Hz was applied to the cell and change in transmittance was measured by a photomultiplyer. As a result, a double hysteresis peculiar to the antiferroelectric phase was observed in a temperature region of from 90° C. to −2° C.

Figure 2:
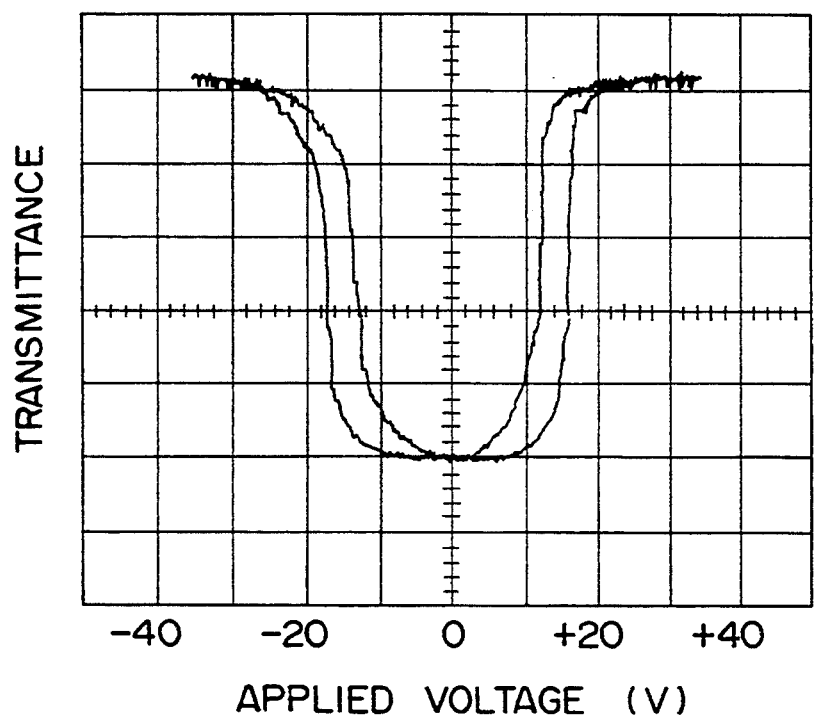
FIG. 2 is a graph showing optical response of the liquid crystal compound (4) in Example 1.

An optical response hysteresis at 70° C. is shown in FIG. 2.

EXAMPLES 2 to 4

In the same way as in Example 1, a compound of formula $C_mH_{2m+1}O—C_6H_4—C_6H_4—COO—C_6H_4—COO—C^*H(C_2H_5)C_6H_{13}$ wherein m is 9, 11 or 12 was produced, and identification of phases was conducted by observation of a texture and measurement with DSC.

Phase transition temperatures of the compounds are as shown in Table 1. They were found to have an antiferroelectric phase.

In the same way as in 5) of Example 1, optical response of these compounds was measured, and they were found to have a double hysteresis peculiar to the antiferroelectric phase.

of a texture and measurement with DSC. As a result, the following phase transition temperatures are shown.

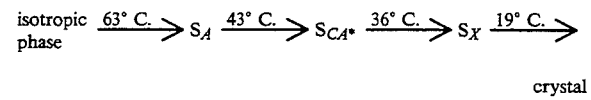

In the same way as in 5) of Example 1, optical response of this compound was measured, and a double hysteresis peculiar to an antiferroelectric phase was shown.

EXAMPLE 6

Production of 4-(1-ethylheptyloxycarbonylbiphenyl) 4'-n-decyloxyphenyl-4-carboxylate [In formula (1), R=C$_{10}$H$_{21}$, X=—O—, K=1, L=2, n=6]

1) Production of 4'-acetoxy-4-(1-ethylheptyloxycarbonyl)biphenyl (1)

Ten milliliters of thionyl chloride were added to 2.5 g of 4'-acetoxy-4-biphenylcarboxylic acid, and the mixture was refluxed for 6 hours. Then, excess thionyl chloride was completely evaporated. The resulting acid chloride was dissolved in 50 ml of toluene, and 5 ml of pyridine was further added. S-(+)-3-nonanol (1.5 g) was added dropwise to the solution. The mixture was refluxed for 18 hours, and allowed to cool. One hundred milliliters of dichloromethane were added, and the resulting mixture was allowed to cool, and washed with hydrochloric acid, a sodium hydroxide aqueous solution and water in this sequence. After drying, the solvent was removed, and the solid was purified by silica gel column chromatography to obtain 2.5 g of a final product.

2) Production of 4'-hydroxy-4-(1-ethylheptyoxycarbonyl)biphenyl (2)

Fifteen milliliters of ethanol and 1.2 g of benzylamine were added to the above compound (1), and the mixture was stirred at room temperature for 24 hours. Fifty milliliters of dichloromethane were added, and the mixture was washed with hydrochloric acid and water. After drying, the solvent was removed, and the solid was purified by silica gel column chromatography to obtain 2.1 g of a final product.

3) Production of 4-(1-ethylheptyloxycarbonylbiphenyl) 4'-n-decyloxyphenyl-4-carboxylate (3)

TABLE 1

| Example No. | m | Phase transition temperature of $C_mH_{2m+1}O—C_6H_4—C_6H_4—COO—C_6H_4—COO—C^*H(C_2H_5)C_6H_{13}$ |
|---|---|---|
| 2 | 9 | crystal $\xleftarrow{11° C.}$ SCA* $\xleftarrow{84° C.}$ SA $\xleftarrow{132° C.}$ isotropic phase |
| 3 | 11 | crystal $\xleftarrow{0.7° C.}$ SCA* $\xleftarrow{90° C.}$ SA $\xleftarrow{102° C.}$ isotropic phase |
| 4 | 12 | crystal $\xleftarrow{41° C.}$ SCA* $\xleftarrow{89° C.}$ SA $\xleftarrow{99° C.}$ isotropic phase |

SX is unidentified liquid crystal phase.

EXAMPLE 5

Production of 4-(1-ethylheptyloxycarbonylphenyl) 4'-n-decylbiphenyl-4-carboxylate [In formula (1), R=C$_{10}$H$_{21}$, X=—(single bond), K=2, L=1, n=6]

A final product was produced in the same way as in Example 1 except using 4'-decylbiphenyl-4-carboxylic acid instead of 4'-decyloxybiphenyl-4-carboxylic acid. Identification of phases was conducted by observation p-Octylbenzoic acid (1.2 g) was chlorinated with 10 ml of thionyl chloride in the same way as in (1). Twenty milliliters of toluene and 4 ml of pyridine were added to the obtained acid chloride, and 1 g of the compound (2) was then added. The mixture was refluxed for about 20 hours, and allowed to cool, followed by adding 50 ml of dichloromethane. The resulting mixture was washed with hydrochloric acid, a sodium hydroxide aqueous solution and water in this sequence, and dried to remove the solvent. The solid was purified by silica gel column chromatography to obtain 6 g of a final product.

Identification of phases was carried out by observation of a texture and measurement with DSC.

Phase transition temperatures of the compound (3) of this invention are as follows.

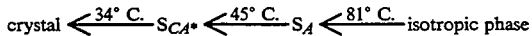

4) In the same way as in 5) of Example 1, optical response of this compound was measured, and a double hysteresis peculiar to an antiferroelectric phase was shown.

EXAMPLE 7

Production of 4-(1-ethylpentyloxycarbonylphenyl) 4'-decyloxybiphenyl-4-carboxylate [In formula (1), R=$C_{10}H_{21}$, X=0, K=2, L=1, n=4]

A final product was produced in the same way as in Example 1 except using S-(+)-3-heptanol instead of S-(+)-3-nonanol as an optically active alcohol. Identification of phases of this compound was conducted by observation of a texture and measurement with DSC. As a result, the following phase transition temperatures are shown. Presence of an antiferroelectric phase was thus confirmed.

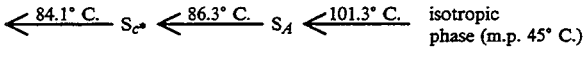

In the same way as in 5) of Example 1, optical response of this compound was measured, and a double hysteresis peculiar to an antiferroelectric phase was shown.

Figure 3:
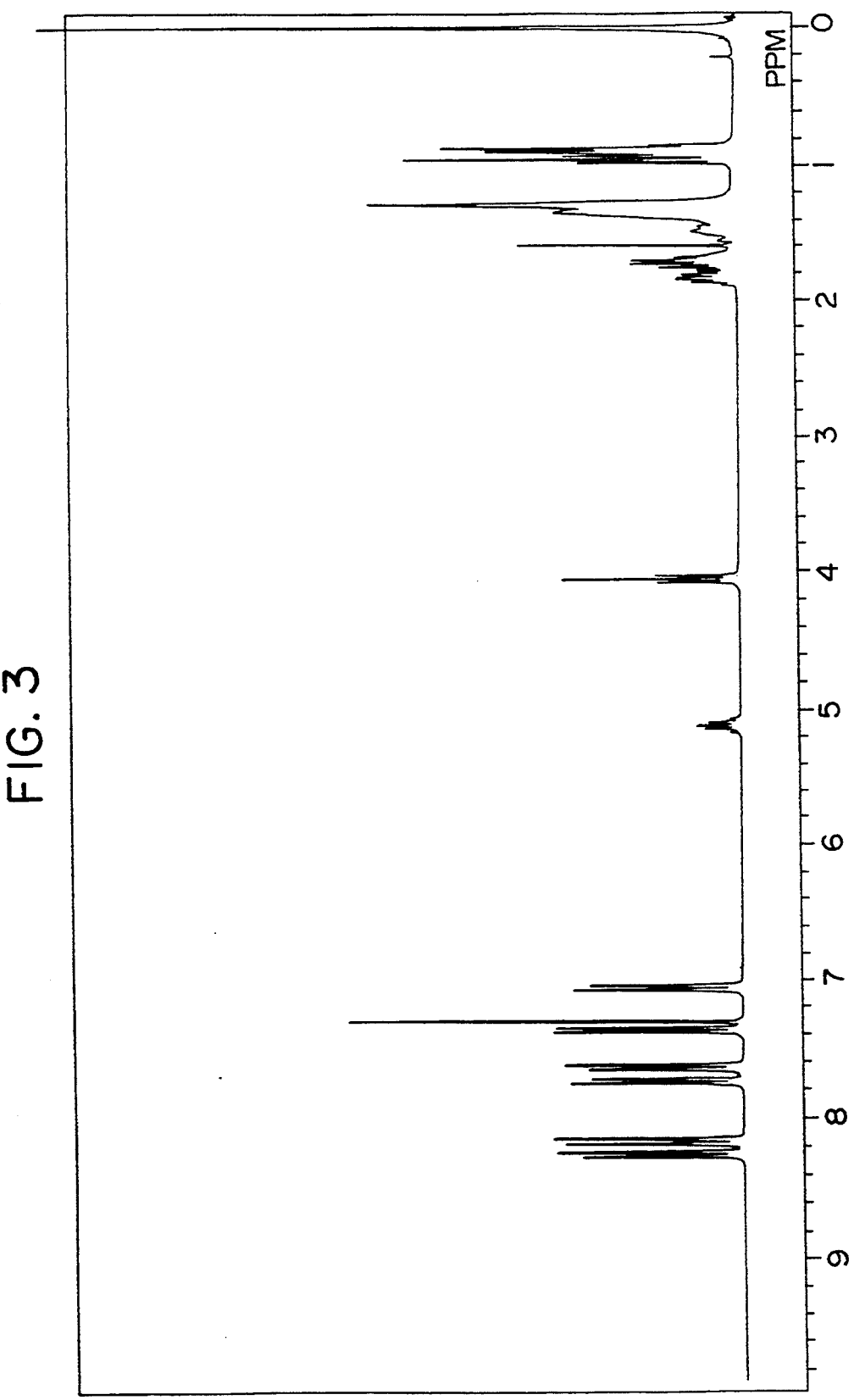
FIG. 3 is an NMR spectrum of a liquid crystal compound in Example 7.

An NMR spectrum of the final product is shown in FIG. 3.

EXAMPLE 8

Production of 4-(1-ethylnonyloxycarbonylphenyl) 4'-decyloxybiphenyl-4-carboxylate [In formula (1), R=$C_{10}H_{21}$, X=0, K=2, L=1, n=8]

A final product was produced in the same way as in Example 1 except using S-(+)-3-undecanol instead of S-(+)-3-nonanol as an optically active alcohol. Identification of phases of this compound was conducted by observation of a texture and measurement with DSC. As a result, the following phase transition temperatures are shown. Presence of an antiferroelectric phase was thus confirmed.

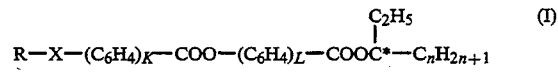

In the same way as in 5) of Example 1, optical response of this compound was measured, and a double hysteresis peculiar to an antiferroelectric phase was shown.

Figure 4:
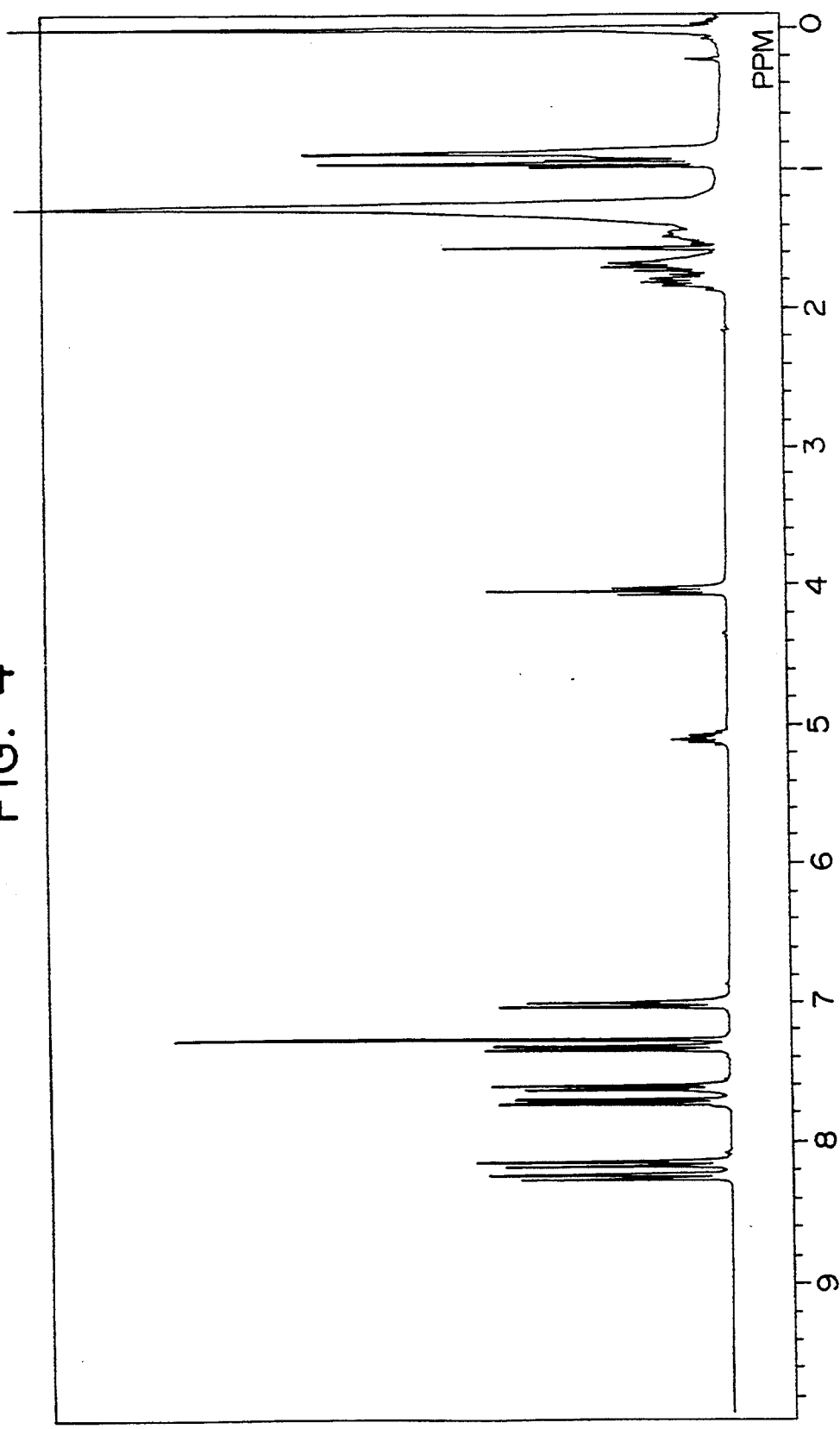
FIG. 4 is an NMR spectrum of a liquid crystal compound in Example 8.

An NMR spectrum of the final product is shown in FIG. 4.

What we claim is:

1. An antiferroelectric liquid crystal compound represented by formula (I)

$$R-X-(C_6H_4)_K-COO-(C_6H_4)_L-COOC^*(C_2H_5)-C_nH_{2n+1} \quad (I)$$

wherein
R denotes $C_9H_{19}$, $C_{10}H_{21}$, $C_{11}H_{23}$ or $C_{12}H_{25}$ and
when R denotes $C_{10}H_{21}$, X denotes a single bond or an oxygen atom, and
when X denotes an oxygen atom, (i) K=1, L=2 and n is 6 or (ii) K=2, L=1 and n is 4, 6 or 8, and when
X denotes a single bond, K=2, L=1 and n=6, and when R denotes $C_9H_{19}$, $C_{11}H_{23}$ or $C_{12}H_{25}$, X denotes an oxygen atom, K=2, L=1 and n=6, and C* denotes an asymmetric carbon atom.

2. A liquid crystal display device formed from the antiferroelectric liquid crystal compound of claim 1.

* * * * *